June 11, 1974 J. D. SLUSARENKO Plant Pat. 3,567
APPLE TREE
Filed Feb. 12, 1973
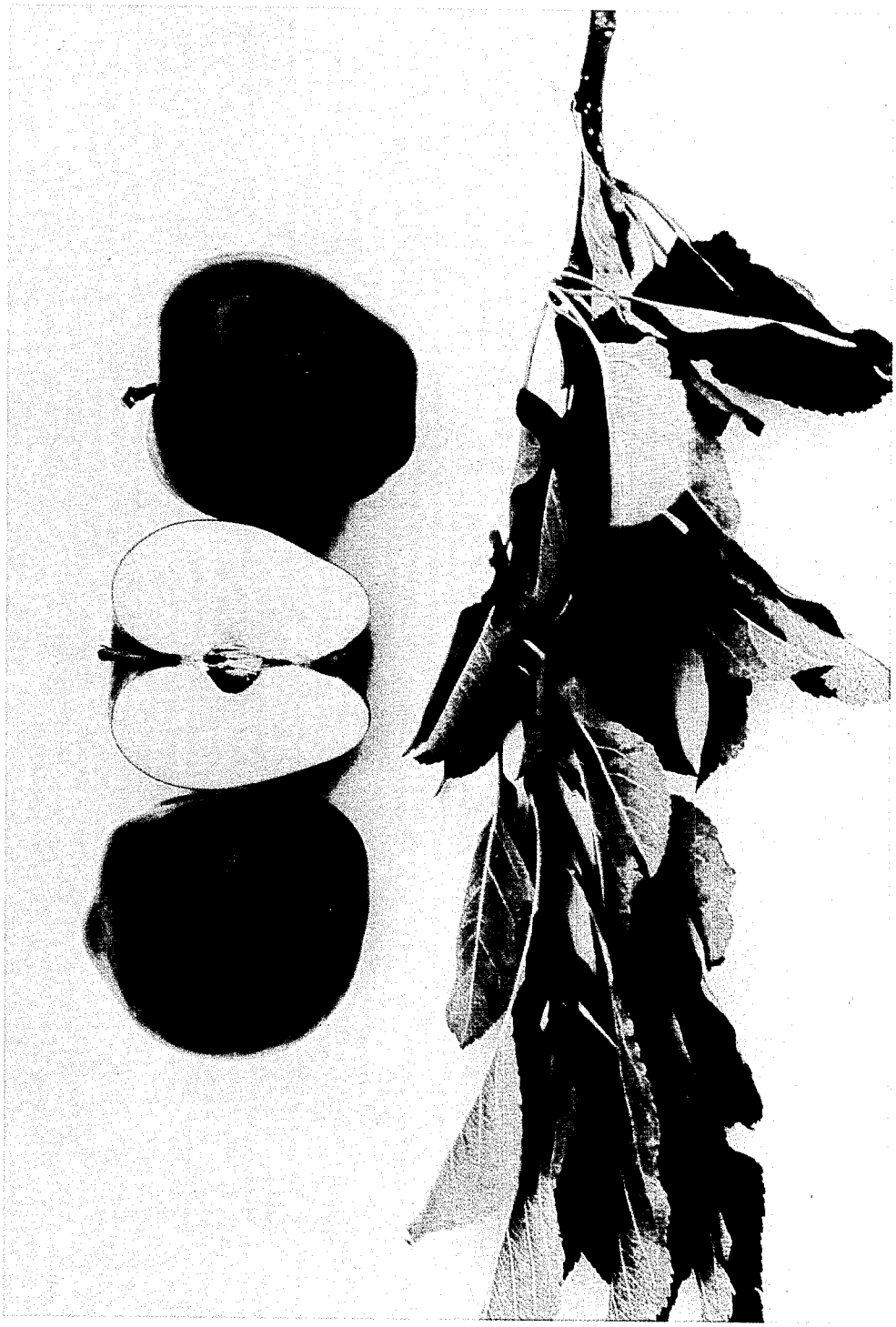

United States Patent Office

Plant Pat. 3,567
Patented June 11, 1974

3,567
APPLE TREE

Jack D. Slusarenko, Milton-Freewater, Oreg., assignor to Stark Bro's Nurseries & Orchards Co., Louisiana, Mo.

Filed Feb. 12, 1973, Ser. No. 331,978
Int. Cl. A01h *5/03*
U.S. Cl. Plt.—35 1 Claim

The present invention relates to a new and distinct variety of apple tree which was discovered by me as bud sport of an unknown strain of the apple variety known as "Red Delicious" (unpatented), said discovery having been made by me in my cultivated orchard located at Milton-Freewater, Oreg.

Extensive observations and tests of the new sport and progeny thereof propagated by me on established orchard trees by grafting in my orchard aforementioned, have convinced me that the sport is a new and distinct variety of apple tree which generally resembles the "Super Starking Delicious" variety—Frank strain (Plant Pat. No. 2,440) which has been widely distributed by my assignee under the registered trademark "Starking," but bears fruit which develops full red color well in advance of internal maturity and about four days earlier than the fruit of the "Super Starking Delicious" variety, thereby attaining better demand on the early market at premium prices.

The accompanying drawing shows typical specimens of the foliage and fruit of my new apple variety, with one of the fruit specimens being shown in cross-section, and all as depicted in color.

The following is a detailed description of the new variety, with color terminology in accordance with Ridgway's Color Standards and Nomenclature (hereinafter abbreviated as (R)), Munsell Color Chart (hereinafter abbreviated as (M)), and the Horticultural Colour Guide (hereinafter abbreviated as (HCG)), except where general color terms of ordinary dictionary significance are obvious:

Locality where grown and observed: Milton-Freewater, Oreg.

Parentage: Sport of an unknown strain of the variety "Red Delicious."

Dates of first and last picking: About Sept. 1 and Sept. 7, respectively.

Tree: Medium large; vigorous; spreading; tall; vase-formed; rapid-growing; hardy; productive; regular bearer.

*Trunk.*—Medium slender; smooth.

*Branches.*—Medium slender; smooth; little-branched. Color—Buffy Brown, Plate XL, Color No. 17''', tone i (R). Lenticels—Medium few; medium small.

*Leaves.*—Medium large; medium narrow; medium long; oval; taper-pointed; thick; rugose. Length—From about 3½ inches to 4 inches. Width—About 1⅞ inches. Color—Ivy Green, Plate 000/060/1, page 200, Vol. 2 (HCG). Margin—Coarsely serrate. Petiole—Medium long; thick.

Flowers: Medium early; medium large.

*Dates of first and full bloom.*—About Apr. 20 and Apr. 30, respectively.

*Color.*—White.

Fruit:

*Maturity when described.*—Eating ripe (about Mar. 1).

*Size.*—Fairly uniform; conical; angular. Axial diameter—From about 3¼ inches to 4 inches. Transverse diameter—From about 3⅛ inches to 3¾ inches.

*Cavity.*—Symmetrical; rounded toward apex; acute; even; pubescent toward apex. Depth—About ¾ inch. Breadth—About 1¼ inches. Markings—Dark Greenish Yellow, Hue 7.5 Y 6/7 (M).

*Basin.*—Symmetrical; rounded; wide; furrowed. Depth—About ½ inch. Breadth—About 1 inch. Markings—None.

*Stem.*—Stout. Length—From about 1 inch to 1⅛ inches. Breadth—About 3/32 inch. Markings—None.

*Calyx.*—Closed; segments persistent; broadly lanceolate; acute; about ¼ inch long; approximate at base; prostrate; refluxed from base at apex, converged from base toward center; both outer and inner surfaces pubescent.

*Skin.*—Thick, tough; smooth; glossy. Dots—Obscure; many; even; ruptured; circular. Color of dots—White. Distribution of dots—Most numerous toward basin. Color markings—Striped; self-colored; bright. Color—Garnet Lake, Plate 828, page 172, Vol. 2 (HCG), with light stripes af Scarlet, Plate 19/1, page 19, Vol. 1, (HCG). Bloom—Wanting. Scarfskin—Wanting. General color effect—All over deep red, with few lighter red stripes.

*Flesh.*—Juicy. Color—White, with yellowish tint. Texture—Firm; tender; fine; crisp. Flavor—Mild. Quality—Good.

*Core.*—Median. Bundle area—Medium small; cordate; symmetrical at base; acute at base; halves of area—equal. Bundles—Inconspicuous, in one whorl; color—Yellowish. Core lines—Clasping. Cross section—Indistinct. Carpellary area—Indistinct; small. Calyx tube—Pubescent toward base, funnel-form; stem of funnel—long; depth of tube to shoulder—about ½ inch; entire depth—about ¾ inch. Styles—Present; united toward base; pubescent throughout. Stamens—In one whorl; median. Auxiliary cavity—Present. Seed cells—Closed; cell walls—distant, thin, tough; longitudinal section—broadly obovate, obtuse at apex; surface—fissured, tufted; cross section—broad.

Seeds: Usually 7; no more than 2 per cell.

*Length.*—About ⅝ inch.

*Breadth.*—About 5/16 inch.

*Form.*—Acute.

*Color.*—Seal Brown, Plate XXXIX, Color No. 5''', tone m (R).

Use: Market; dessert.

Keeping quality: Good; about 120 days in ordinary storage.

I claim:

1. A new and distinct variety of apple tree, substantially as herein shown and described, characterized particularly as to novelty by its general resemblance to the apple variety "Super Starking Delicious"—Frank strain (Plant Pat. No. 2,440), but the fruit of which develops a full red color at least four days earlier than the fruit of "Super Starking Delicious," with consequent earlier marketability and at premium price values.

No references cited.

ROBERT E. BAGWILL, Primary Examiner